US007138564B2

(12) United States Patent
Tian et al.

(10) Patent No.: US 7,138,564 B2
(45) Date of Patent: Nov. 21, 2006

(54) **ISOLATED *AMARANTHUS* AGGLUTININ GENE AND USES THEREOF**

(75) Inventors: Yingchuan Tian, Beijing (CN); Yonggang Zhou, Beijing (CN); Hongnian Guo, Beijing (CN)

(73) Assignee: Institute of Microbiology Chinese Academy of Sciences, Beijing (CN)

( * ) Notice: Subject to any disclaimer, the term of this patent is extended or adjusted under 35 U.S.C. 154(b) by 318 days.

(21) Appl. No.: 10/399,240

(22) PCT Filed: Nov. 5, 2001

(86) PCT No.: PCT/CN01/01533

§ 371 (c)(1),
(2), (4) Date: Apr. 14, 2003

(87) PCT Pub. No.: WO02/36775

PCT Pub. Date: May 10, 2002

(65) Prior Publication Data

US 2004/0023270 A1 Feb. 5, 2004

(30) Foreign Application Priority Data

Nov. 3, 2000 (CN) ................................ 00 1 33426

(51) Int. Cl.
*C12N 15/09* (2006.01)
*C12N 15/29* (2006.01)
*C12N 15/82* (2006.01)
*C12N 15/00* (2006.01)
*A01H 5/00* (2006.01)

(52) U.S. Cl. ...................... 800/278; 800/278; 800/298; 800/295; 435/69.1; 435/320.1; 435/468; 536/23.6

(58) Field of Classification Search ............... 536/23.6; 435/468, 320.1, 69.1; 800/278, 298, 295
See application file for complete search history.

(56) References Cited

U.S. PATENT DOCUMENTS 5,670,635 A * 9/1997 Datta et al. ................ 536/23.6
5,846,736 A * 12/1998 Datta et al. .................. 435/7.1

OTHER PUBLICATIONS

Thomas Transue, "The Crystal Structures of Two Spermadhesins Reveal the CUB domain Fold", Nature Structural Biology, vol. 4, No. 10, Oct. 1997, pp. 779-783.

The QIAexpressionist, "A handbook for high-level expression and Purification of 6xHIS-tagged proteins", Jan. 2000, 4th Edition, 1997 Novagen Catalog, pp. 36-39.

Andrew Paterson et al., A Rapid Method for Extraction of Cotton (Gossypium spp.) Genomic DNA Suitable For RFLP or PCR Analysis, Plant Molecular Biology Reporter, vol. 11 (2) 1993, pp. 122-127.

Yvan Rahbe et al., Toxicity of Lectins and Processing of Ingested Proteins in the Pea Aphid Acyrthosiphon pisum, Entomologia Experimentalis of Applicata, vol. 76 (1995) pp. 143-155.

C.R. Boland, Use of the Lectin from *Amaranthus caudatus* as a Histochemical Probe of Proliferating Colonic Epithelial Cells, Cancer Research, vol. 51, Jan. 15, 1991, pp. 657-665.

Noel D. Vietmeyer, "Lesser-Known Plants of Potential Use in Agriculture and Forestry", Science, vol. 232, Articles, Jun. 13, 1986, pp. 1379-1384.

Anjana Raina et al., "Molecular Cloning of a Gene Encoding a Seed-Specific Protein with Nutritionally Balanced Amino Acid Composition from *Amaranthus*", Proc. Natl. Acad. Sci USA, vol. 89, pp. 11774-11778, Dec. 1992, Plant Biology.

U.K. Laemmli, "Cleavage of Structural Proteins During the Assembly of the Head of Bacterophage T4", Nature, vol. 227, Aug. 15, 1970, pp. 680-685.

Genpept, Javascript, Chain B, Crystal Structures of *Amaranthums caudatus* Agglutinin Protein, Jul. 23, 1997, NCBI, ,4 pages.

Li T-Y et al., Science in China (B series), (1994), 24:276-282, Example 6, Chinese Version of Journal (Chinese Version) with attached 37:1479-1488 (English Version).

Sambrook et al., "Molecular Cloning, A Laboratory Manual", Cold Spring Harbor Laboratory Press, 1993, Example 3 (Chinese Version) with attached "Molecular Cloning" 1989, (English Version).

* cited by examiner

*Primary Examiner*—Medina A. Ibrahim
(74) *Attorney, Agent, or Firm*—Ann S. Hobbs; Venable LLP (57) ABSTRACT

The present invention provides the cloning of intron-containing *Amaranthus caudatus* agglutinin (ACA) gene from *Amaranthus caudatus* and the coding region gene sequence encoding the ACA protein. The said gene sequence of the ACA gene coding region was ligated with highly efficient and stable microbial expression vectors to produce the ACA protein using microbe largely. High expression of the ACA gene can make the transgenic plants have antiaphid activity and improve the nutrition quality thereof. The ACA gene has potential application value in plant anti-insect gene engineering and quality improvement.

10 Claims, 8 Drawing Sheets

Fig.1

1
ATGGCGGGATTACCAGTGATTATGTGCCTAAAATCAAATAACAACCAG

AAGTACTTAAGATATCAAAGTGATAATATTCAACAATATGGTCTTCTT

CAATTTTCAGCTGATAAGATTTTAGATCCATTAGCTCAATTTGAAGTC

GAACCTTCCAAGACTTATGATGGTCTTGTTCACATCAAATCTCGCTAC

ACTAACAAATATTTGGTTAGgtacgttttttttcgcgtttatacttcc tccgtttcaatatagtcgcaatatatcgaaaataaacactattcactt atctcctttaatttgtgattgataagtaatttataagttaaaacatag tcaactgagatcttgtttgattcatctcgacgtaaagattattaatat caaattttataatttttatattatacataattgtagttattaatgatt gaattagtacattagactgcgtgaaaaaggcatatgttgtaagtattt tggaacgaaggtagtgttatatttcttctgttagtctatttaaaattt gcgatatttaaattaaatatttaagatttttttgagttacatgtttca aattctggagtgagtacgtactttaagtatacttttgtactagctacc atttgattgacataattaataaatgggaaattccacatggtagcatct agttttgatgaaatgccagtggtgacacttttttaagaaaattccaca tgctagcattcagtttatacactatctaattgccgtagcattttccgt taagttcttgttaaattccactaaatttatcattttgtaagttttttt ccacatggtagtatccagttttgttaatttatcattttaactcttaa ttcaccattttaatgtttaattcactatttaattcattaacgctcata agtgttagatattttattgaaaaattataagaaactatctaatcggg tcgaaacaagaacttattcgcctatttttcgatacgtaaaccggaaaa

Fig. 2A gatatttggcgtcattttacctatcataacgattttttcaataaac ggacgttgcaattacccttatgggataactctttcgaaaatccggtcg aaacaagtacttattcgcctattttccgatagatgtgttcaagaaaat gggacaactaaatagattcagagggagtatttcggagtaattatgttg acaaaattatacttgaactaatagctacggtgatgcttgttcaatttc actgattttgtacaatcataaagtttcttgatcacatttccaaaaaaa tgaaagttaagtggcaaaaaatatgtgaatataaaatttgacaagtct aatttaaaattttcactaatttttttaataaaacgaaatacaacata atatattttattgagatatattttgtgaaatttaatttaaatgtcac cactataaatttgtaatggtacatatagttgatttagttacatttatt agaccttctagctgcataattaaaatcatactaaagcttttcctgag atagaatctaatgatatttctcatatgccggcatgcaaccaaataaag tgttactatataaattactaaagtagcgacattttttaatgttgcaaa aagaaaatttgtttagtgacggtcttatagtgtgactatctctattg ggcagacatatgtacatttagtatgaaatgatcacttataattttaaa gtaatacaattacagagtgacttgtttacaatgaatttgtgtttttgt ccagcaagtcttttaatgagagacgtctcttagatctaatccattaga gtttaattcttactcttattctatattttctttatgggtcacccaat tagagttggtatctcaaagagaccgtctctcacaagaatttgcgtttt tgtcttagGTGGTCTCCCAATCATTATTGGATTACAGCATCAGCCAAT

GAACCAGATGAAAATAAAAGCAATTGGGCATGCACATTATTCAAACCA

Fig.2B

CTTTACGTAGAAGAAGGTAACATGAAAAAGGTTCGACTTTTGCACGTC

CAATTAGGTCATTATACACAGAATTATACCGTTGGTGGGTCCTTCGTA

TCATACTTATTTGCCGAATCAAGTCAAATTGATACCGGCTCTAAAGAC

GTATTCCATGTCATAGATTGGAAATCAATCTTTCAATTTCCCAAAAGA

TATGTCACATTTAAAGGAAATAATGGAAATATTTAGGGGTTATCACA

ATTAATCAACTTCCATGTCTACAATTTGGGTATGATAATCTTAATGAT

CCAAAGGTGGCTCATGAAATGTTTGTCACTTCTAATGGTACTATTTGC

ATTAAATCCACTTATATGAACAAGTTTTGGAGACTCTCTACGGATGAT

TGGATATTAGTCGATGGGAATGATCCTCGCGAAACTAATGAAGCTGCA

GCGTTGTTTAGGTCAGATGTGCATGATTTAATGTGATTTCGCTTTTG

AACATGCAAAAACTTGGTTTATTAAGAGATTTACGAGTGGTAAGCCT

GGGTTTATAAATTGTATGAATGCAGCTACTCAAAATGTTGATGAAACT
                                           2628
GCTATTTTAGAGATAATAGAATTGGGATCCAACAAC

```
  1  X A G L P V I M C L K S N N H Q K Y L R Y Q S D N I Q Q Y G    ACA.pro
  1  M A G L P V I M C L K S N N N Q K Y L R Y Q S D N I Q Q Y G    ACAc.pro 31  L L Q F S A D K I L D P L A Q F E V E P S K T Y D G L V H I    ACA.pro
 31  L L Q F S A D K I L D P L A Q F E V E P S K T Y D G L V H I    ACAc.pro 61  K S R Y T N K Y L V R W S P N H Y W I T A S A N E P D E N K    ACA.pro
 61  K S R Y T N K Y L V R W S P N H Y W I T A S A N E P D E N K    ACAc.pro 91  S N W A C T L F K P L Y V E E G N M K K V R L L H V Q L G H    ACA.pro
 91  S N W A C T L F K P L Y V E E G N M K K V R L L H V Q L G H    ACAc.pro 121  Y T Q N Y T V G G S F V S Y L F A E S S Q I D T G S K D V F    ACA.pro
121  Y T Q N Y T V G G S F V S Y L F A E S S Q I D T G S K D V F    ACAc.pro 151  H V I D W K S I F Q F P K G Y V T F K G N N G K Y L G V I T    ACA.pro
151  H V I D W K S I F Q F P K R Y V T F K G N N G K Y L G V I T    ACAc.pro 181  I N Q L P C L Q F G Y D N L N D P K V A H Q M F V T S N G T    ACA.pro
181  I N Q L P C L Q F G Y D N L N D P K V A H E M F V T S N G T    ACAc.pro 211  I C I K S N Y M N K F W R L S T D D W I L V D G N D P R E T    ACA.pro
211  I C I K S I Y M N K F W R L S T D D W I L V D G N D P R E T    ACAc.pro 241  N E A A A L F R S D V H D F N V I S L L N M Q K T W F I K R    ACA.pro
241  N E A A A L F R S D V H D F N V I S L L N M Q K T W F I K R    ACAc.pro 271  F T S G K P G F I N C M N A A T Q N V D E T A I L E I I G L    ACA.pro
271  F T S G K P G F I N C M N A A T Q N V D E T A I L E I I G L    ACAc.pro 301  G Q N N                                                        ACA.pro
301  G S N N                                                        ACAc.pro
```

ISOLATED *AMARANTHUS* AGGLUTININ GENE AND USES THEREOF

FIELD OF THE INVENTION

This invention relates to the field of plant gene engineering for insect-resistance and biochemistry. Particularly, it relates to a newly cloned *Amaranthus caudatus* agglutinin (ACA) gene and the recombinant plasmids for conducting the expression of ACA gene in plants. Transgenic plants having aphid-resistance can be obtained from the transformation of plants with the said recombinant plasmids. Meanwhile, ACA protein could be produced using microbes harboring a high efficient and stable microbe expression vector for ACA gene.

BACKGROUND OF THE INVENTION

*Amaranthus caudatus* agglutinin (ACA) is a kind of phytoagglutinin (plant lectin) present in the seeds of *Amaranthus caudatus* having high nutritive value originated in South America continent [Vietmeyer, N. et al (1986), Science 232:1379–1384] and is mainly as a storage protein providing nutrition during the seed germination. ACA is abundantly synthesized in seeds during the formation of endosperm, but little in vegetative organs. The amino acid sequence of ACA protein has been reported in GenBank (Accession No. g2781234). Rahbe Y. et al carried out in vitro feeding pea aphids (*Acyrthosiphon pisum*) with different purified plant lectin proteins and the results showed that ACA gave the very high inhibition or toxic effect for tested aphids [Rahbe Y, Sauvion N, Febvay G et al 1995, Entomol Exp Appl, 76:143–155]. It is reported that this agglutinin plays an important role in specific recognition of tumor cells, histochemical identification and early diagnosis of tumors [Boland, C. et al, (1991), Cancer Res. 51:657–665]. As the function of plant agglutinins being further elucidated and potential application values thereof in medicine and biology being understood, it appears necessary to clone the ACA gene for studying and applying the agglutinin. Though the aphid-resistant activity of ACA has been revealed in the insect-resistant test in vitro as described, this activity has not been verified in transgenic plants expressing ACA gene. Moreover, ACA protein as a protein being rich in essential amino acid residues may play an important role in improving quality of crop. High level expression of ACA protein obtained in vitro conveniently could be a sufficient supply of this protein for identification of some tumor diseases.

BRIEF DESCRIPTIONS OF THE INVENTION

Based on the above situation, the purpose of this invention is to provide a novel structural gene of ACA protein, its recombinant plasmid and recombinant plasmid expressed in microbe and plants.

In order to obtain the structural gene of ACA, the structural gene of ACA was first obtained by polymerase chain reaction (PCR) using total DNA from *A. caudatus* as template. The gene consists of 2628 bp (SEQ ID NO:1) including an intron of 1716 bp and two exons of 212 bp (SEQ ID NO:2) and 700 bp (SEQ ID NO:3) respectively. High sequence homology between the amino acid sequence (SEQ ID NO:4) deduced from the nucleotide sequence thereof and the reported amino acid sequence of ACA protein reported by transue et al[Nature Structural Biology, 1997, 4(10): 779–783] exists. A recombinant plasmid which can drive the ACA gene constitutively expressed in plants was constructed. The advantage thereof is that the recombinant plasmid can express the ACA protein in all tissues of the resulted transgenic plants. For expression of the ACA gene in particular tissue, a tissue-specific promoter could be used to make the ACA protein specifically be synthesized in the target tissue of transgenic plants. This type of expression of ACA protein could make the transgenic plants resistant to aphid efficiently. At the same time, since ACA protein is rich in essential amino acids, its high expression in transgenic plants could improve the nutritive value of the plants. An efficient and stable expression vector is constructed and abundant ACA protein could be synthesized in recombinant microbes, the protein could have certain application in tumor-detection.

The ACA gene is firstly cloned by this invention, this makes it possible to produce ACA in large quantity and to apply this agglutinin in agriculture and medicine.

In order to achieve the above purposes, the particular procedures leading to this invention were as follows: A pair of PCR primers were designed and synthesized according to the cDNA sequence of AmAl protein of *Amaranthus hypochondriacus* [Raina A et al. (1992). PNAS, Vol(89): 11774–11778], which is highly homologous in amino acid sequence with ACA protein. ACA structural gene was amplified by PCR in the presence of genomic DNA extracted from seeds or leaves of *A. caudatus* and cloned. The purified PCR product was ligated with pUC18 vector and then transformed into *E. coli* DH5α to obtain the recombinant plasmid pACA containing ACA structural gene and *E. coli* DH5α transformant thereof. The transformant (pACA/DH5α) named pACAg/DH5α. was deposited in the China General Microbiological Culture Collection Center with accession No. CGMCC NO.0438. A pair of PCR primers were designed according to the sequence of the recombinant plasmid pACA which was used as a template, the DNA fragment in the coding region of cDNA of ACA was amplified by reverse PCR, and then transformed into *E. coli* DH5α after self-ligation to obtain the recombinant plasmid pACAc and the *E. coli* DH5α transformant thereof. DNA fragments of the cDNA and ACA structural gene were isolated from recombinant plasmid pACAc and pACA, and ligated with plant constitutive expression vector pBin438 respectively and then transformed into *E. coli* DH5α to obtain recombinant plasmids pBACAc and pBACA that can express constitutively in plant and *E. coli* DH5α transformant. Agrobacterium tumefaciens LBA4404 was transformed with recombinant plasmid pBACAc and PBACA extracted from the above transformants to obtain *A. tumefacieus* transformants pBACAc/LBA4404 and pBACA/LBA4404 respectively. At the same time, the DNA fragment of the ACA structural gene was isolated from the recombinant plasmid pACAc and ligated with *E. coli* expression vector pET30a(+), then transformed into *E. coli* BL21(DE3) to obtain a recombinant plasmid pEACAc that can express in *E. coli* and *E. coli* transformant pEACAc/BL21 (DE3). The *E. coli* transformant pEACAc/BL21(DE3) can express a specific ACA protein upon induction.

BRIEF DESCRIPTION OF THE DRAWINGS

The attached drawings are presented to further illustrate this invention in detail.

DETAILED DESCRIPTION OF THE PREFERABLE EXAMPLES

Further detailed description of this invention is presented via particular examples and the attached figures.

EXAMPLES

1. Isolation of Total DNA from *Amaranthus Caudatus* Plants

Seeds of *Amaranthus caudatus* were kindly provided by Regional Plant Introduction Station of USDA, IOWA State University. The procedure of DNA isolation was referred to Paterson A H, Brubaker C L, Wendel J F et al [Plant Mol. Biol. Reporter, 1993, 11(2): 122–127] with some modifications. Two hundreds mg of leaves from *Amaranthus caudatus* plants or seeds that is maturing were ground into powder in liquid nitrogen and 1 ml of DNA extraction buffer [0.35 M glucose, 0.1 M Tris-HCl (PH8.0), 0.005 M Na2-EDTA (PH8.0), 2% (W/V) polyvinyl-pyrolidone (PVP40), 0.1% (W/V) diethylithiocabarmic acid (DIECA), 0.2% (W/V) mercaptoethanol, 0.5% Triton-X100] prechilled with ice was added. After mixed thoroughly, the suspension was centrifuged at 4° C., 2700×g for 10 mins to remove the supernatant. To the resulted pellet, 500 µl of nuclear lysis buffer [0.1 M Tris-HCl, PH8.0, 1.4 M NaCl, 0.02 M Na2-EDTA (PH8.0), 2% (W/V) CTAB (hexadecy1triammonium bromide), 2% (W/V) PVP, 0.1% (W/V) DIECA, 0.2% (W/V) mercaptoethanol, 0.5% Triton-X100] was added for re-suspension of the pellet at 65 ° C. for 30 mins. The resuspension was extracted with equal volume of chloroform-isoamyl alcohol (24:1) and to the resulted supernatant (the up-phase) after centrifugation at 10000 rpm, 0.6 vol of pre-cold isopropanol was added to precipitate DNA. After centrifugation at 12000 rpm, the precipitate was washed with 70% ethanol, dried at room temperature and dissolved in 50 µl sterilized water and stored at −20° C.

2. PCR Amplification of the ACA Gene

Twenty µl of a PCR system consisted of 1 µl of about 50 ng total DNA from *Amaranthus caudatus,* 2 µl 10×PCR buffer, 2 µl dNTP (the final concentration for each NTP is 10 mmol/L), 2 µl each of the two primers (final concentration is 10 pmol/µl), Taq Plus I (2.5 Units), the rest volume was made up with deionized water. The reaction system was covered with proper amount of mineral oil to prevent evaporation.

```
5' primer sequence:
5'-GGA AGA TCT ACC ATG GCG GGA TTA CCA GTG-3'

3' primer sequence:
5'-AGC GTC GAC TTA GTT GTT GGA TCC CAA TTC-3'
```

The reaction condition is: pre-denaturing at 94° C. for 3 mins, and then 94° C. 1 min, 49° C. for 1 min, 72° C. 1 min 30 sec, with 30 cycles, an elongation of 10 mins at 72° C., was preformed after the 30 cycles reaction. The PCR products were separated by electrophoresis and two DNA fragments of 2.5 kb and 0.9 kb were isolated. Recovery of the two fragments was performed using the DNA recovery kit available from Shanghai Huashun Ltd and dissolved in 30 µl sterilized water.

3. Cloning and Sequencing of the ACA Gene

Figure 1:
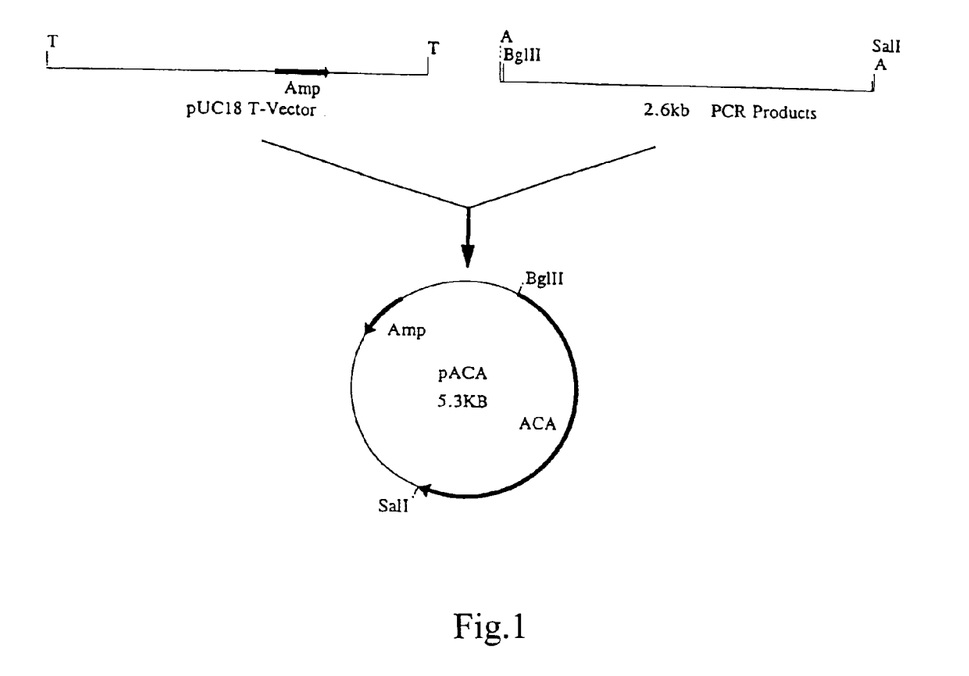
FIG. 1: Construction of a recombinant plasmid pACA of the ACA gene (Amp: ampicillin resistance)
Figure 2A:
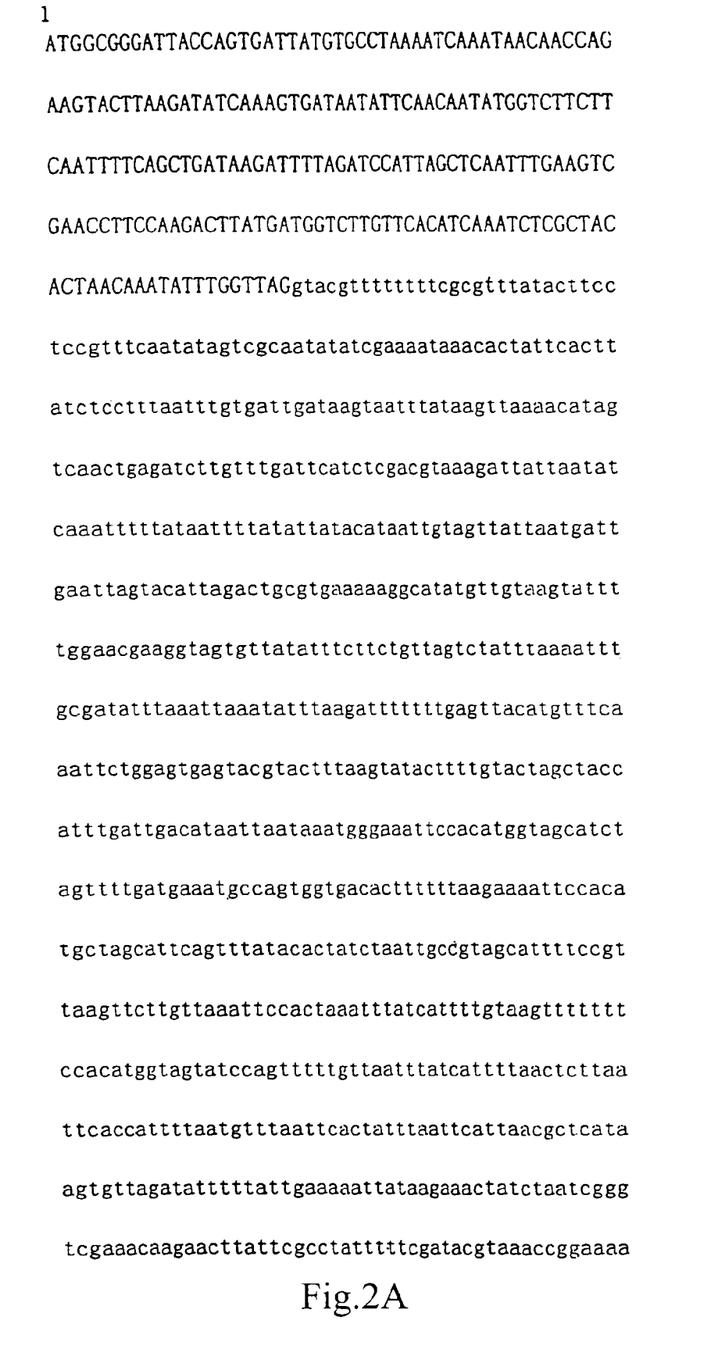
FIG. 2: Total length nucleotide sequence as SEQ ID NO:1 of the ACA gene, letters in lower case represent the nucleotide sequence of the intron.
Figure 2B:
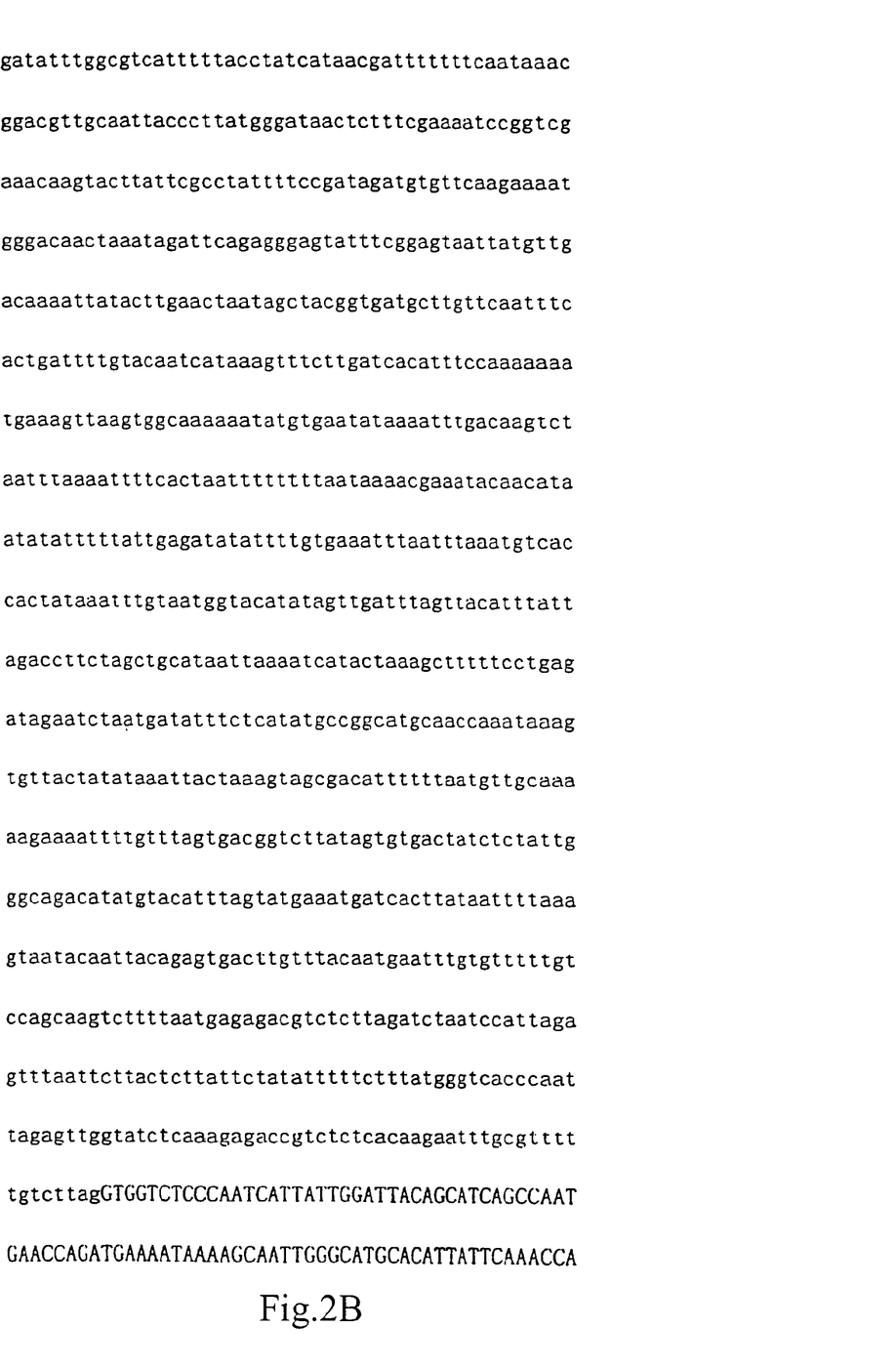
Figure 2C:
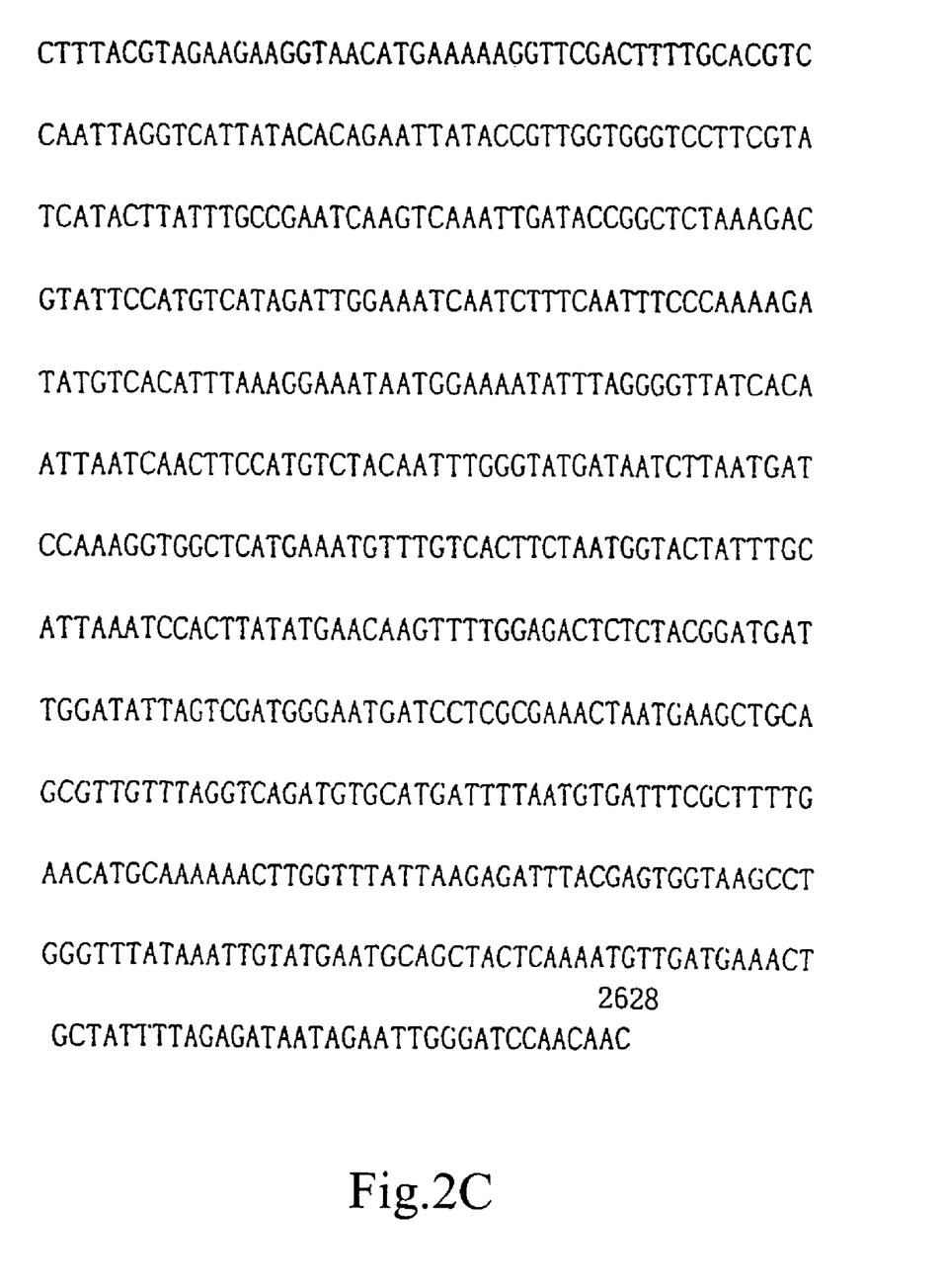
Figure 3:
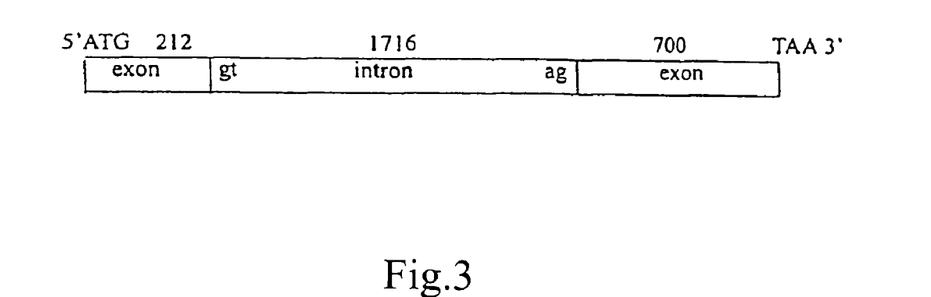
FIG. 3: Sketch map of the ACA gene structure, numbers on the map indicate the size of corresponding region in base pairs.

Methods for DNA clone and sequencing referred to <<Molecular Cloning, A Laboratory Manual>> edited by Sambrook J. et al., Cold Spring Harbor Laboratory Press, 1993. 10 µl of the recovered PCR product was ligated with 1 µl of pUC18-T vector in 20 µl of ligation system comprising 2 µl of 10×ligation buffer, 10 µl of PCR product, 1 µl of vector, 1 µl of T4 DNA ligase and 6 µl of water. The ligation reaction was performed at 14° C.~16° C. for 12 hours. *E.coli* DH5α competent cells was transformed with 8 µl of the ligation mixture and then spreaded onto the LB solid medium containing 50 mg/L Amp (ampicillin). The positive colonies were selected using blue-white colony screening method. The plasmids of selected positive colonies were extracted and further identified by restriction enzyme digestion and sequencing analysis using Pharmacia T7 DNA Sequencing Kit. The results confirmed the insertion of the 2.6 kb ACA gene. The construction process of the recombinant plasmid is shown in FIG. 1, named as pACA. The complete nucleotide sequence of the ACA gene was analyzed on an ABI 377 DNA sequencer and the result is shown in FIG. 2. The result from sequence analysis indicate that the ACA gene having the DNA sequence of SEQ ID NO:1 is consisted of 2628 bp, containing an intron of 1716 bp and two exons of 212 bp (SEQ ID NO:2) and 700 bp (SEQ ID NO:3) respectively. The structure of the ACA gene is shown in claim 1 and diagramed in FIG. 3.

4. Coding Sequence of the ACA Gene Obtained by Reverse PCR

Based on the sequence of the ACA gene (SEQ ID NO:1), two primers complemented with the exons adjacent to the intron respectively were designed and synthesized. The sequences of the two primers were as followes:

```
5' end sequence: 5'-GTG GTC TCC CAA TCA TTA TTG-3'

3' end sequence: 5'-CTA ACC AAA TAT TTG TTA GTG-3'
```

Reverse PCR was performed in a total volume of 20 µl containing 1 µl dNTP (10 mmol/L each); 1 µl of each primer (25 pmol/µl); 1 µl of the diluted pACA solution as template (pACA extracted from *E. coli* transformant by alkaline lysis method was diluted 500 fold); 2 µl of 10×PCR buffer, 0.4 µl of pfu Taq DNA polymerase (5unit/µl), the final volume was made up with sterilized water. The reaction condition is: pre-denaturing at 94° C. for 3 mins, and then 94° C. 50 sec, 58° C. for 50 sec, 72° C. 2 mins 30 sec, with 30 cycles, an elongation of 10 mins at 72° C. was preformed after the 30 cycles reaction. The PCR product showed a 3.5 kb DNA in size on Agarose gel electrophoresis. The PCR product was purified and then phosphorylated by T4 polynucleotide kinase. After precipitated with ethanol, the DNA pellet was dissolved in 20 µl sterilized water.

5. Cloning and Sequencing of the Coding Region of the ACA Gene

Figure 4:
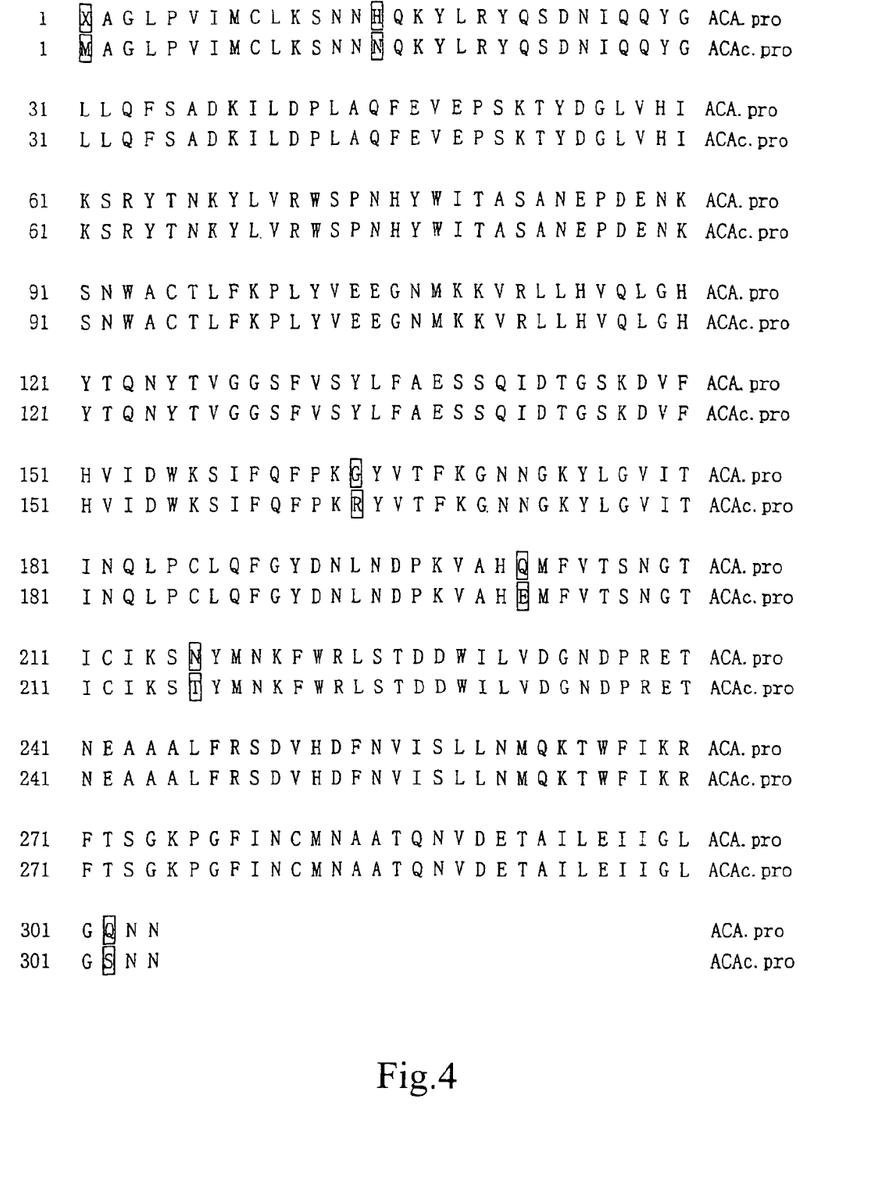
FIG. 4: Homologous comparison of amino acid sequence of the ACA protein deduced from the nucleotide sequence of ACA gene with the amino acid sequence of the ACA protein reported (ACA.PRO: amino acid sequence of the ACA protein (SEQ ID NO:5); ACAc.PRO: Amino acid sequence deduced from the cloned ACA gene of the invention (SEQ ID NO:4); amino acids in boxes indicate the differences between the two sequences)

2 µl of 10×ligation buffer, 1 µl T4-DNA ligase (1 Unit/µl) and 7 µl of sterilized water was added to 10 µl of the above purified product, the final volume was 20 µl. The reaction mixture was incubated at 14~16° C. for 12 hours. Competent cells of *E. coli* DH5α was transformed with 8 µl of the ligation mixture and spreaded onto the LB solid medium containing 50 mg/L Amp. Plasmids in the selected transformants were isolated using alkaline lysis method and a 900 bp fragment was produced after digestion with Nco I and Sal I as expected. The recombinant plasmid is designated as pACAc. The coding sequence in pACAc was verified by sequence analysis on an ABI 377 DNA sequencer. The coding sequence of ACA gene (SEQ ID NO:2 and SEQ ID NO:3) in pACAc is shows in FIG. 2 (represented by capital letters). Comparison of the amino acid sequence (SEQ ID NO:4) encoded by ACA gene with that of the published ACA sequence is shown in FIG. 4.

6. Construction of Plant Expression Vector for ACA Gene Coding Sequence and Preparation of Recombinant *Agrobacterium Tumefacieus*.

Figure 5:
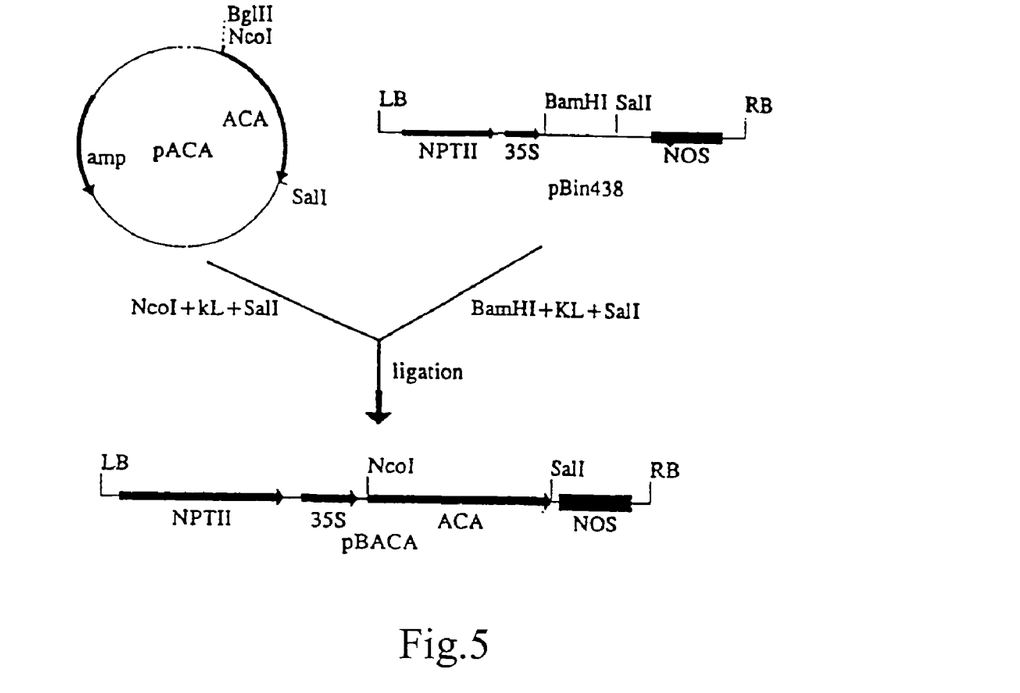
FIG. 5: Construction of plant expression vector PBACA for ACA gene (NPTII: Neomycin phosphotransferase gene; 35S: CaMV 35S promoter with double enhancer sequences; NOS: Transcription terminator sequence of nopaline synthase gene; LB: T-DNA left border of Ti plasmid; RB: T-DNA right border sequence of Ti plasmid)

Plasmid pACAc was digested by Bgl II and Sal I. The fragment of the ACA structural gene was recovered and then ligated with the fragment of the vector pBin438 digested by BamH I and Sal I [Li T-Y, et al, Science in China (B series), (1994) 24: 276–282] to construct the recombinant plasmid pBACAc, as outlined in FIG. 5. After transformation of *E. coli* competent cells with the ligation mixture, the cells were spreaded onto the LB solid medium containing 50 mg/L Kan(kanamycin). The recombinant plasmid was identified by restriction enzyme digestion and PCR method. Purified pBACAc using alkaline lysis method was transformed into competent cells of *Agrobacterium tumefacieus* LBA4404, the cells were spreaded onto the YEP solid medium containing 50 µg/µl Kan, 50 µg/µl Rif(rifampin), 50 µg/µl Str(streptomycin). The selected single colony was analyzed by restriction enzyme digestion and PCR detection to obtain the tranformant of *Agrobacterium tumefacieus* LBA4404 containing pBACAc.

7. Construction of Plant Expression Vector Containing the ACA Gene

Figure 6:
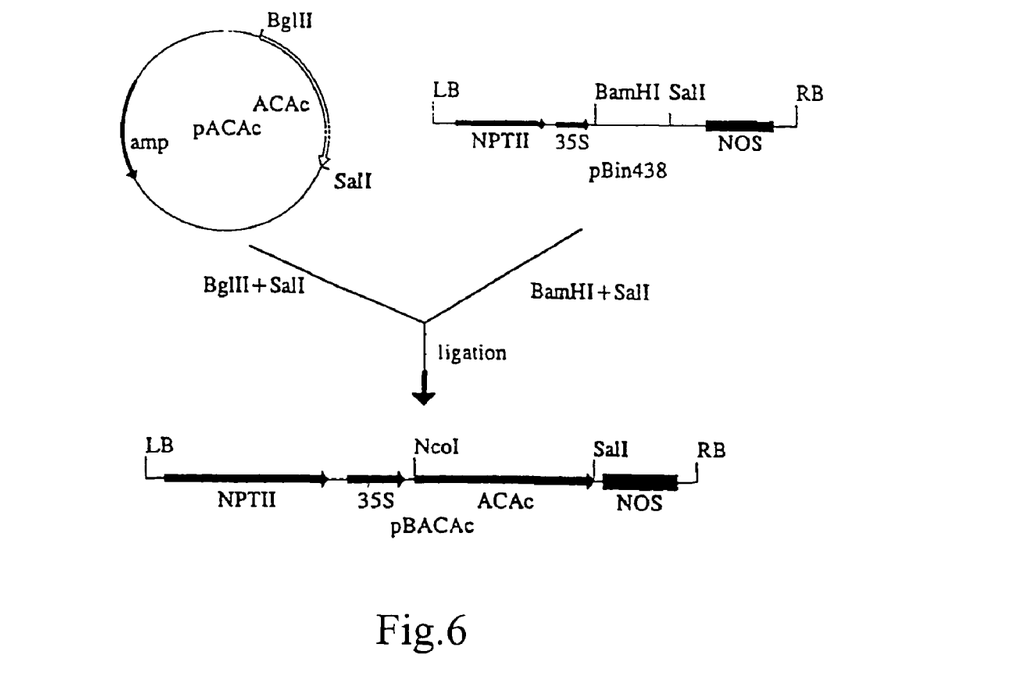
FIG. 6: Construction of plant expression vector pBACAc for ACA gene coding region (Kl: Kienow DNA polymerase)

The ACA gene fragment from pACA was digested by Nco I, filled in the cohesive ends with klenow DNA polymerase and then digested by Sal I to obtain a 2.6 kb of gene fragment. The isolated fragments were ligated with vector pBin438 fragment digested by BamH I and then filled in with klenow followed by digested with Sal I to form recombinant plasmid pBACA. The ligation mixture was transformed into competent cells of *E. coli* DH5α and the recombinant plasmids in the transformants selected were identified by restriction enzyme digestion and PCR detection. The preparation of *Agrobacterium tumefacieus* was as the same with that of described in above 6. Besides CaMV 35S promoter, tissue-specific promoters or other kind of promoters could be used to construct a plant expression vector with the ACAc or ACA gene. The construction process was shown in FIG. 6.

8. Construction of a Expression Vector for ACAC Gene and its Expression in *E. coli*.

Figure 7:
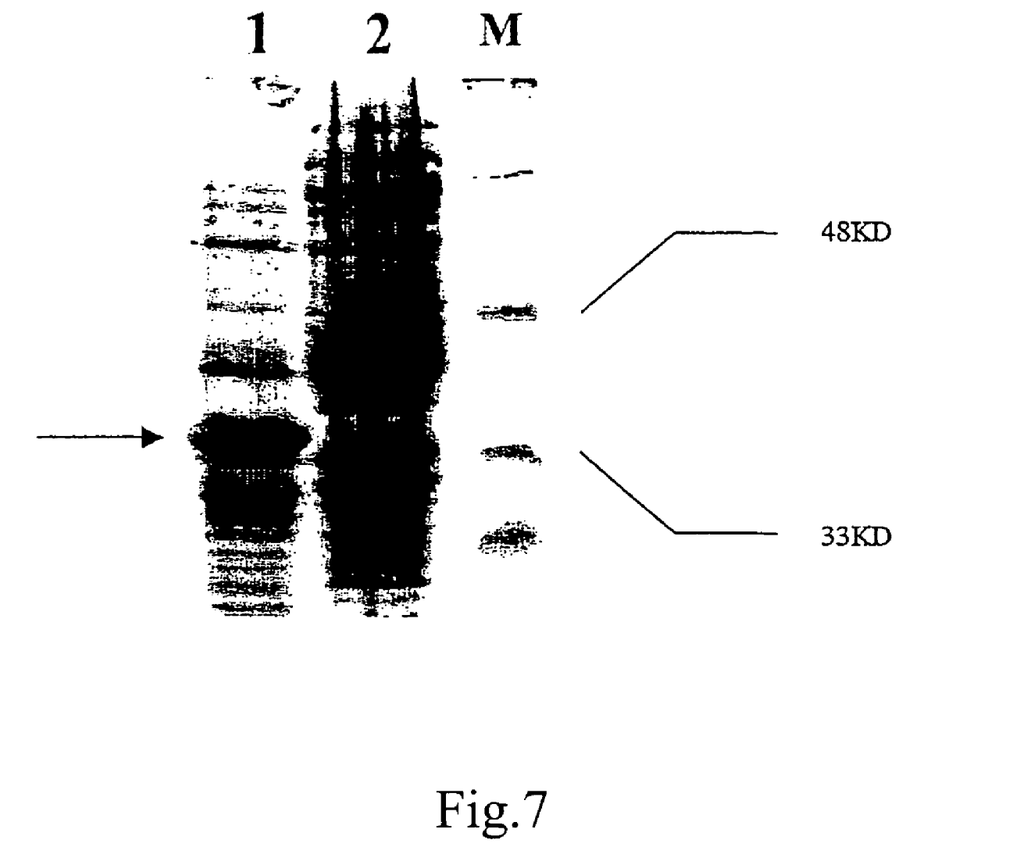
FIG. 7: SDS-PAGE pattern of *E. coli* expression products of the ACA protein [M: Protein molecular weight standard; 1: pEACAc/BL21(DE3) 2: pET30a/BL21(DE3); Arrowhead points the position of the expressed target protein (ACA)]

The plasmid pACAc was digested by Nco I/Sal I. About 0.9 kb fragment was recover and then ligated with a expression vector pET30a (+) digested by the same enzymes. The recombinant plasmid named as pEACAc was used to transform *E. coli* BL21 (DE3) cells. Induced expression of the ACA gene was achieved based on the procedure provided by Qiagene Company[A handbook for high-level expression and purification of 6×His-Taged protein]. A single colony of pEACAc transformants was inoculated into liquid LB medium containing 50 µg/µl kamamycin and cultured at 37° C. with shaking at 250 rpm. When the bacteria grow to OD=0.2, isopropyl-β-D-thiogalactoside (IPTG) was added to a final concentration of 1 mmol/L. The culture was shaked continually in the same condition for 3h. Total protein of the bacterial cells was analyzed by SDS-PAGE as described by Laemmli UK. (Nature 227:680–685, 1970) using pre-stained protein marker from BioLab as protein MW standard. Results from SDS-PAGE showed that a 36 kD specific protein was produced in pEACAc transformant (FIG. 7, lane 1) while this protein is absent in *E. coli* BL 21 (DE3) cells (FIG. 7, Lane 2), indicating that the ACA protein was expressed in *E. coli*. The expression level of the ACA protein is estimated to be 35% of total bacterial proteins based on the calculation of gel-scanning. SDS-PAGE pattern was shown in FIG. 7.

Notes:

LB medium: 5 g/L NaCl; 10 g/L Trypton; 5 g/L Yeast extract; PH7.0; 12 g/L Agar; Autoclaved at 15 pound for 30 mins.

YEP medium: 5 g/L NaCl; 10 g/L Trypton; 10 g/L Yeast extract; PH7.0; 12 g/L Agar, Autoclaved at 15 pound for 30 mins.

The invention claimed is:

1. An isolated gene having the nucleotide sequence of SEQ ID NO: 1.

2. A recombinant plasmid comprising the nucleotide sequence of SEQ ID NO: 1.

3. A recombinant plasmid comprising the nucleotide sequence of SEQ ID NO: 2 and the nucleotide sequence of SEQ ID NO: 3.

4. A recombinant microbe comprising the recombinant plasmid of claim 2, wherein the recombinant microbe is *Eschenchia coli* DH5α deposited under the Accession number CGMCC 0438.

5. A method of producing *Amaranthus caudatus* agglutinin protein comprising transforming a host cell with an expression vector comprising the nucleotide sequence of SEQ ID NO: 2 and the nucleotide sequence of SEQ ID NO: 3; and culturing the transformed host cell for the production of the protein.

6. A transgenic plant comprising the recombinant plasmid of claim 2.

7. A method of producing *Amaranthus caudatus* agglutinin protein comprising transforming a host cell with an expression vector comprising the nucleotide sequence of SEQ ID NO: 1; and culturing the transformed host cell for the production of the protein.

8. A transgenic plant comprising the recombinant plasmid of claim 3.

9. A host cell transformed with the recombinant plasmid of claim 2.

10. A host cell transformed with the recombinant plasmid of claim 3.

* * * * *

SEQUENCE LISTING

<160> NUMBER OF SEQ ID NOS: 4

<210> SEQ ID NO 1
<211> LENGTH: 2628
<212> TYPE: DNA
<213> ORGANISM: Amaranthus caudatus

<400> SEQUENCE: 1

-continued

```
atggcgggat taccagtgat tatgtgccta aaatcaaata acaaccagaa gtacttaaga      60
tatcaaagtg ataatattca acaatatggt cttcttcaat tttcagctga taagatttta     120
gatccattag ctcaatttga agtcgaacct tccaagactt atgatggtct tgttcacatc     180
aaatctcgct acactaacaa atatttggtt aggtacgttt tttttcgcgt ttatacttcc     240
tccgtttcaa tatagtcgca atatatcgaa aataaacact attcacttat ctcctttaat     300
ttgtgattga taagtaattt ataagttaaa acatagtcaa ctgagatctt gtttgattca     360
tctcgacgta aagattatta atatcaaatt tttataattt tatattatac ataattgtag     420
ttattaatga ttgaattagt acattagact gcgtgaaaaa ggcatatgtt gtaagtattt     480
tggaacgaag gtagtgttat atttcttctg ttagtctatt taaaatttgc gatatttaaa     540
ttaaatattt aagattttt tgagttacat gtttcaaatt ctggagtgag tacgtacttt     600
aagtatactt ttgtactagc taccatttga ttgacataat aataaatgg gaaattccac      660
atggtagcat ctagttttga tgaaatgcca gtggtgacac ttttttaaga aaattccaca     720
tgctagcatt cagtttatac actatctaat tgccgtagca ttttccgtta agttcttgtt     780
aaattccact aaatttatca ttttgtaagt ttttttccac atggtagtat ccagttttg      840
ttaatttatc atttaactc ttaattcacc attttaatgt ttaattcact atttaattca      900
ttaacgctca taagtgttag atatttttat tgaaaaatta taagaaacta tctaatcggg     960
tcgaaacaag aacttattcg cctatttttc gatacgtaaa ccggaaaaga tatttggcgt    1020
catttttacc tatcataacg attttttttca ataaacggac gttgcaatta cccttatggg   1080
ataactcttt cgaaaatccg gtcgaaacaa gtacttattc gcctattttc cgatagatgt    1140
gttcaagaaa atgggacaac taaatagatt cagagggagt atttcggagt aattatgttg    1200
acaaaattat acttgaacta atagctacgg tgatgcttgt tcaatttcac tgattttgta    1260
caatcataaa gtttcttgat cacatttcca aaaaaatgaa agttaagtgg caaaaaatat    1320
gtgaatataa aatttgacaa gtctaattta aaattttcac taattttttt taataaaacg    1380
aaatacaaca taatatattt ttattgagat atattttgtg aaatttaatt taaatgtcac    1440
cactataaat ttgtaatggt acatatagtt gatttagtta catttattag accttctagc    1500
tgcataatta aaatcatact aaagcttttt cctgagatag aatctaatga tatttctcat    1560
atgccggcat gcaaccaaat aaagtgttac tatataaatt actaaagtag cgacatttt    1620
taatgttgca aaaagaaaat tttgtttagt gacggtctta tagtgtgact atctctattg    1680
ggcagacata tgtacattta gtatgaaatg atcacttata attttaaagt aatacaatta    1740
cagagtgact tgtttacaat gaatttgtgt ttttgtccag caagtctttt aatgagagac    1800
gtctcttaga tctaatccat tagagtttaa ttcttactct tattctatat ttttctttat    1860
gggtcaccca attagagttg gtatctcaaa gagaccgtct ctcacaagaa tttgcgtttt    1920
tgtcttaggt ggtctcccaa tcattattgg attacagcat cagccaatga accagatgaa    1980
aataaaagca attgggcatg cacattattc aaaccacttt acgtagaaga aggtaacatg    2040
aaaaaggttc gacttttgca cgtccaatta ggtcattata cacagaatta taccgttggt    2100
gggtccttcg tatcatactt atttgccgaa tcaagtcaaa ttgataccgg ctctaaagac    2160
gtattccatg tcatagattg gaaatcaatc tttcaatttc ccaaaagata tgtcacattt    2220
aaaggaaata atggaaaata tttaggggtt atcacaatta atcaacttcc atgtctacaa    2280
tttgggtatg ataatcttaa tgatccaaag gtggctcatg aaatgtttgt cacttctaat    2340
ggtactattt gcattaaatc cacttatatg aacaagtttt ggagactctc tacggatgat    2400
```

-continued

```
tggatattag tcgatgggaa tgatcctcgc gaaactaatg aagctgcagc gttgtttagg      2460
tcagatgtgc atgattttaa tgtgatttcg cttttgaaca tgcaaaaaac ttggtttatt      2520
aagagattta cgagtggtaa gcctgggttt ataaattgta tgaatgcagc tactcaaaat      2580
gttgatgaaa ctgctatttt agagataata gaattgggat ccaacaac                  2628
```

<210> SEQ ID NO 2
<211> LENGTH: 212
<212> TYPE: DNA
<213> ORGANISM: Amaranthus caudatus
<220> FEATURE:
<221> NAME/KEY: Exon 1 of Amaranthus caudatus agglutinin structure gene
<222> LOCATION: (1)..(212)
<223> OTHER INFORMATION:

<400> SEQUENCE: 2

```
atggcgggat taccagtgat tatgtgccta aaatcaaata caaccagaa gtacttaaga       60 tatcaaagtg ataatattca acaatatggt cttcttcaat tttcagctga taagatttta    120
gatccattag ctcaatttga agtcgaacct tccaagactt atgatggtct tgttcacatc    180
aaatctcgct acactaacaa atatttggtt ag                                  212
```

<210> SEQ ID NO 3
<211> LENGTH: 700
<212> TYPE: DNA
<213> ORGANISM: Amaranthus caudatus
<220> FEATURE:
<221> NAME/KEY: Exon 2 of Amaranthus caudatus agglutinin structure gene
<222> LOCATION: (1)..(700)
<223> OTHER INFORMATION:

<400> SEQUENCE: 3

```
gtggtctccc aatcattatt ggattacagc atcagccaat gaaccagatg aaaataaaag      60
caattgggca tgcacattat tcaaaccact ttacgtagaa gaaggtaaca tgaaaaaggt    120
tcgacttttg cacgtccaat taggtcatta tacacagaat tataccgttg gtgggtcctt    180
cgtatcatac ttatttgccg aatcaagtca aattgatacc ggctctaaag acgtattcca    240
tgtcatagat tggaaatcaa tctttcaatt tcccaaaaga tatgtcacat ttaaaggaaa    300
taatggaaaa tatttagggg ttatcacaat taatcaactt ccatgtctac aatttgggta    360
tgataatctt aatgatccaa aggtggctca tgaaatgttt gtcacttcta atggtactat    420
ttgcattaaa tccacttata tgaacaagtt ttggagactc tctacggatg attggatatt    480
agtcgatggg aatgatcctc gcgaaactaa tgaagctgca gcgttgttta ggtcagatgt    540
gcatgatttt aatgtgattt cgcttttgaa catgcaaaaa acttggtttta ttaagagatt    600 tacgagtggt aagcctgggt ttataaattg tatgaatgca gctactcaaa atgttgatga    660
aactgctatt ttagagataa tagaattggg atccaacaac                          700
```

<210> SEQ ID NO 4
<211> LENGTH: 304
<212> TYPE: PRT
<213> ORGANISM: Amaranthus caudatus
<220> FEATURE:
<221> NAME/KEY: amino acid sequence deduced from the two exons
<222> LOCATION: (1)..(304)
<223> OTHER INFORMATION:

<400> SEQUENCE: 4

```
Met Ala Gly Leu Pro Val Ile Met Cys Leu Lys Ser Asn Asn Asn Gln
1               5                   10                  15
```

-continued

```
Lys Tyr Leu Arg Tyr Gln Ser Asp Asn Ile Gln Gln Tyr Gly Leu Leu
             20                  25                  30

Gln Phe Ser Ala Asp Lys Ile Leu Asp Pro Leu Ala Gln Phe Glu Val
             35                  40                  45

Glu Pro Ser Lys Thr Tyr Asp Gly Leu Val His Ile Lys Ser Arg Tyr
     50                  55                  60

Thr Asn Lys Tyr Leu Val Arg Trp Ser Pro Asn His Tyr Trp Ile Thr
 65                  70                  75                  80

Ala Ser Ala Asn Glu Pro Asp Glu Asn Lys Ser Asn Trp Ala Cys Thr
             85                  90                  95

Leu Phe Lys Pro Leu Tyr Val Glu Glu Gly Asn Met Lys Lys Val Arg
            100                 105                 110

Leu Leu His Val Gln Leu Gly His Tyr Thr Gln Asn Tyr Thr Val Gly
            115                 120                 125

Gly Ser Phe Val Ser Tyr Leu Phe Ala Glu Ser Ser Gln Ile Asp Thr
        130                 135                 140

Gly Ser Lys Asp Val Phe His Val Ile Asp Trp Lys Ser Ile Phe Gln
145                 150                 155                 160

Phe Pro Lys Arg Tyr Val Thr Phe Lys Gly Asn Asn Gly Lys Tyr Leu
                165                 170                 175

Gly Val Ile Thr Ile Asn Gln Leu Pro Cys Leu Gln Phe Gly Tyr Asp
            180                 185                 190

Asn Leu Asn Asp Pro Lys Val Ala His Glu Met Phe Val Thr Ser Asn
            195                 200                 205

Gly Thr Ile Cys Ile Lys Ser Thr Tyr Met Asn Lys Phe Trp Arg Leu
    210                 215                 220

Ser Thr Asp Asp Trp Ile Leu Val Asp Gly Asn Asp Pro Arg Glu Thr
225                 230                 235                 240

Asn Glu Ala Ala Ala Leu Phe Arg Ser Asp Val His Asp Phe Asn Val
                245                 250                 255

Ile Ser Leu Leu Asn Met Gln Lys Thr Trp Phe Ile Lys Arg Phe Thr
            260                 265                 270

Ser Gly Lys Pro Gly Phe Ile Asn Cys Met Asn Ala Ala Thr Gln Asn
        275                 280                 285

Val Asp Glu Thr Ala Ile Leu Glu Ile Ile Glu Leu Gly Ser Asn Asn
    290                 295                 300
```